United States Patent
Zereshkian

(10) Patent No.: US 10,821,255 B2
(45) Date of Patent: Nov. 3, 2020

(54) PERSONALIZED FORCED AIR PURIFIER

(71) Applicant: Gholam Hossein Zereshkian, Richmond Hill (CA)

(72) Inventor: Gholam Hossein Zereshkian, Richmond Hill (CA)

( * ) Notice: Subject to any disclaimer, the term of this patent is extended or adjusted under 35 U.S.C. 154(b) by 1272 days.

(21) Appl. No.: 14/966,494

(22) Filed: Dec. 11, 2015

(65) Prior Publication Data

US 2017/0165445 A1 Jun. 15, 2017

(51) Int. Cl.
| | |
|---|---|
| *A61M 16/10* | (2006.01) |
| *B01D 47/02* | (2006.01) |
| *A61L 9/22* | (2006.01) |
| *A62B 7/10* | (2006.01) |
| *A62B 18/00* | (2006.01) |
| *A61M 15/02* | (2006.01) |
| *A61L 9/14* | (2006.01) |
| *A62B 9/04* | (2006.01) |
| *C02F 1/46* | (2006.01) |
| *A61M 16/16* | (2006.01) |

(52) U.S. Cl.
CPC .......... *A61M 16/107* (2014.02); *A61L 9/145* (2013.01); *A61L 9/22* (2013.01); *A61M 15/02* (2013.01); *A62B 7/10* (2013.01); *A62B 18/003* (2013.01); *B01D 47/024* (2013.01); *A61L 2209/14* (2013.01); *A61M 16/16* (2013.01); *A62B 9/04* (2013.01); *C02F 1/46* (2013.01)

(58) Field of Classification Search
CPC ....... B01D 47/024; B01D 47/028; A61L 9/22; A61L 9/145; A61M 15/02; A61M 87/10; A61M 87/801; A61M 16/105; A61M 16/107; A61M 16/14; A61M 16/16; A62B 7/10; C02F 1/46; C02F 1/4608
USPC .......................................... 95/57, 63, 64, 71
See application file for complete search history.

(56) References Cited

U.S. PATENT DOCUMENTS

| 4,078,891 | A | * | 3/1978 | Madjar | ................... A61L 9/122 261/DIG. 88 |
|---|---|---|---|---|---|
| 6,106,592 | A | * | 8/2000 | Paranjpe | ................... B03C 3/53 95/65 |
| 6,863,715 | B2 | * | 3/2005 | Ike | ..................... B01D 46/0056 96/233 |
| 2008/0196723 | A1 | * | 8/2008 | Tilley | ...................... A62B 7/10 128/204.23 |
| 2010/0258644 | A1 | * | 10/2010 | Kagawa | ................ C02F 1/4608 236/44 A |
| 2013/0037027 | A1 | * | 2/2013 | Schuller | ................. A62B 18/08 128/204.21 |
| 2017/0028095 | A1 | * | 2/2017 | Ohyama | ............. B01D 47/028 |

* cited by examiner

*Primary Examiner* — Timothy A Stanis
*Assistant Examiner* — Victoria Murphy
(74) *Attorney, Agent, or Firm* — Nasser Ashgriz; UIPatent Inc.

(57) ABSTRACT

The present invention is a portable air purifier device intended to be attached to the belt or to the neck of the user and generate purified air enough to breath easily and adequate to make an air curtain to push a way ambient air. Principle of the operation of this device is to push inlet polluted air through layers of ionized water. Water will absorb particles and copper and silver ion kills possible air born bacteria and produce clean air. The purified air will be then delivered to the face of the user either by a flexible hose to a mask or through several flexible hoses to form an air curtain in front of a user's face.

6 Claims, 8 Drawing Sheets

PERSONALIZED FORCED AIR PURIFIER

FIELD OF THE INVENTION

The present invention relates in general to the field of air purifiers, and in particular to a personalized forced air purifier system and mask.

BACKGROUND OF THE INVENTION

A wide variety of face masks have been developed to protect people from polluted particulate matter and dust. Most of the dust masks have been developed to protect people from larger particulate matters such as sand, wood dust, metal dust or the like. Many filtering masks are designed for removing particles as well as some gasses that may include bacteria or harmful viruses. Filtered masks in the market are not efficient and need high intake pressure, which makes using them difficult, especially for the elderly. These masks are not convenient and they usually cover most of the face. Additionally, they tend to be cumbersome and expensive to manufacture and purchase

SUMMARY OF THE INVENTION

The present invention is an air purifier in combination with a mask or an air curtain to provide clean breathing air. The air purifier comprises of a small container, which can be attached to a belt or hang from the neck of a user. The container is preferably made of a light weight material and includes a top lid, a bottom wall and side walls adapted to house a water absorbing material of any one of sponge, cotton etc, which can be removed to be cleaned. The filter is preferably from a material with strong absorbability and is wetted by water or ionized water. The wet filter has an inlet area and an outlet area. The inlet area of the wet filter is exposed to the ambient air. The container has a plurality of openings on the top lid and plurality of openings on the side walls. The container may have any shape and size. A battery driven air fan is attached to the outlet area of the wet filter to suck the ambient air through the wet filter and exhaust a purified air. In operation, the fan sucks the ambient air passing through the filter in the container and exhausts a clear flow of air.

In another embodiment of the present invention the purifier has an ionization system embedded inside the container. Said container, contains of a water chamber. The ionization system comprises of two plate electrodes to ionize and disinfect the water inside the container. Said electrodes are from a heavy metal, such as a copper-silver alloy. Each electrode is being connected to the power source. Released ions in wet filter act as an electrochemical treatment to kill the bacteria released from the ambient air.

By inhale, the contaminated air is driven into the container and pollution, dust and contaminants of the air are scrubbed by the filter and neutralized by the ionized water. The purified air is then released into the outlet port. A flexible air hose is connected to the outlet-port to carry the purified air into the flexible air hose and guide it to the user's interface.

Fastening means are provided on the side walls of the container to open the top lid of the container and replace the contaminated filter which contains dust and dead bacteria and replace it easily with a new filter. The personal air purifier can be attach to ones belt and secured by a belt buckle, or can be hang on the neck.

The output of the container is connected to a mask with an open outlet through a flexible air hose. Said mask is designed to be mounted on the users chin by chin-attaching means. Said mask is being held onto the users head by standard elastic straps. The flexible air hose contains of plurality of air jets extended to the top surface of the mask. Flexible wearable pipes under the shirt of the user guide the purified air and generate a curtain of purified air in front of the nose and mouth of the user.

The air purifier of the present invention can also be used with a full face cover mask having an opening in front of it to direct the exhale air out of the mask.

The container further comprises of a power source to provide power to the fan.

Said power source is a DC battery or other suitable batteries that can be used as a power source.

The present invention can be used in hospitals to make the patients safer and reduce pandemic air born disease to spread easily. It can be used in dusty areas to filter the air, which is essential especially for people with allergy or asthma.

The present invention can also equipped with a container for medical solutions to treat a variety of diseases. Inhalation solutions are typically aqueous-based formulations and contain therapeutically active ingredients and can used by the present invention.

The present invention can also equipped with a container for applying good smells for the user in public places.

It is an object of the present invention to provide an air purifying mask which is light, non-expensive, easy to use and safe.

It is another object of the present invention to provide such a device which is highly portable and which would be lightweight and inexpensive to construct.

Other objects, features, and advantages of the present invention will be readily appreciated from the following description. The description makes reference to the accompanying drawings, which are provided for illustration of the preferred embodiment. However, such embodiments do not represent the full scope of the invention.

BRIEF DESCRIPTION OF THE DRAWINGS

Embodiments herein will hereinafter be described in conjunction with the appended drawings provided to illustrate and not to limit the scope of the claims, wherein like designations denote like elements, and in which:

DETAILED DESCRIPTION OF PREFERRED EMBODIMENTS

Figure 1:
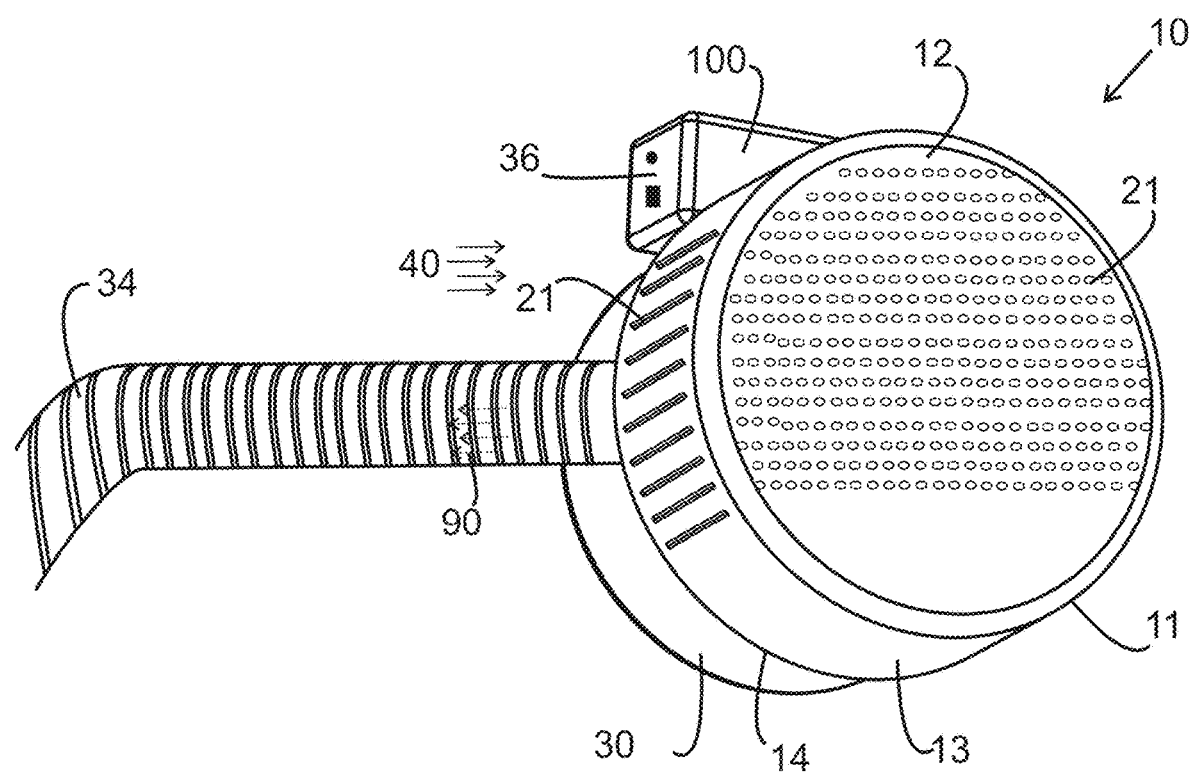
FIG. 1 is a front view of the personalized forced air purifier according to the present invention.
Figure 2:
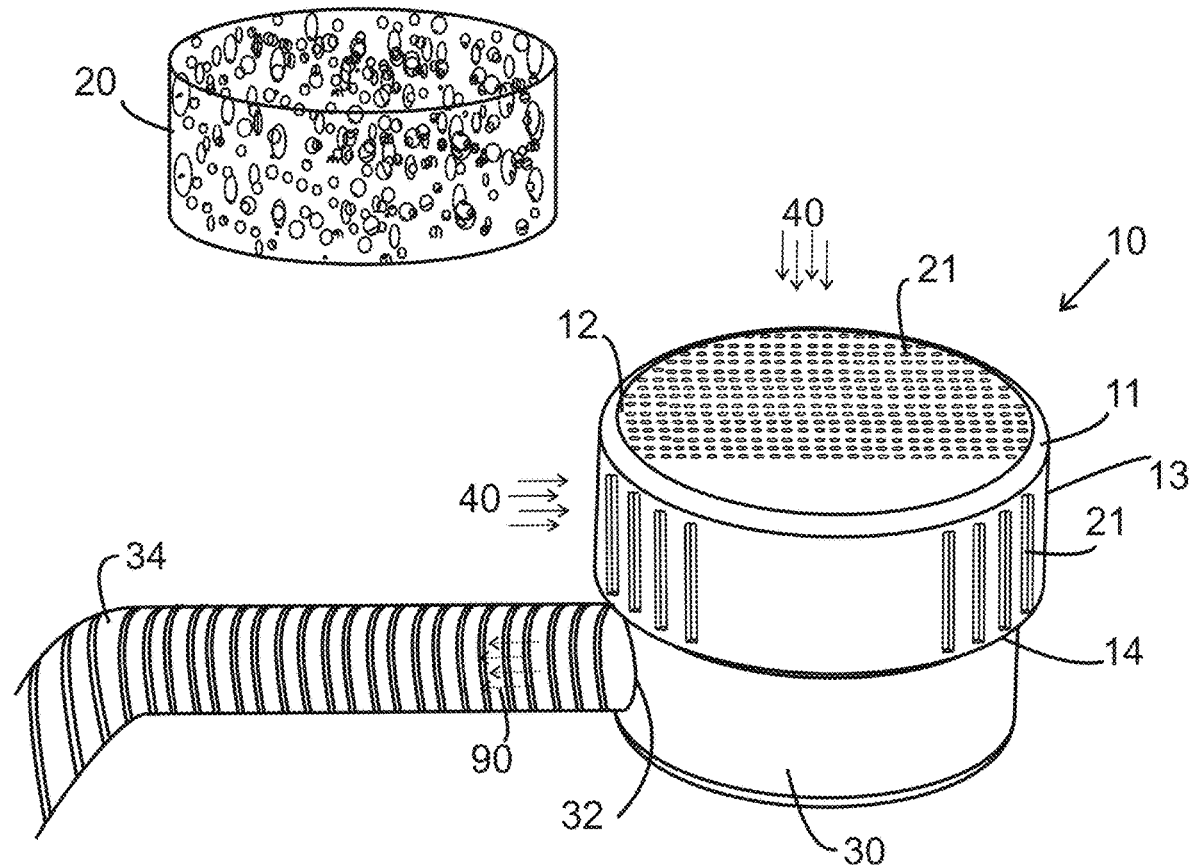
FIG. 2 is a side view of personalized forced air purifier of the present invention and the filter.

Referring to FIGS. 1 and 2, it can be seen that the personalized forced air purifier is a portable wet filter 10 comprises a container 11 preferably made of a light weight material. Said container 11 includes a top lid 12 and a bottom wall 14 and side walls 13. Said container is adapted to house a filter. The top lid 12 has perforations 21 to allow the ambient air 40 to enter into the container for purifying. The lid 12 is fastened on top of the container 11 by a fastening means. There are also openings 21 provided on the side walls 13 of the container 11. The container 11 is adapted to house a sponge like filter. The filter 20 is sponge like material with strong absorbability and is wetted by water or ionized water. The filter 20 can be replaced after contaminated with a clean filter.

A battery driven air fan 30 is attached to the bottom wall 14 of the container 11. The air fan 30 sucks the ambient air 40 through the filter and exhausts a purified air 90 and directs it through an outlet-port to the flexible hose 34. The flexible hose 34 is connected to the outlet-port from one end and to a mask from another end.

A power source 100 is provided on the side wall 13 of the container to provide power to the fan 30. Said power source is a DC battery or other suitable batteries. Li-Ion battery driven fans are readily available which can provide sufficient air flow.

The air purifier 10 is equipped with a control panel 36 to manage the speed of the air fan 30 and the operation of the power source 100.

Figure 3:
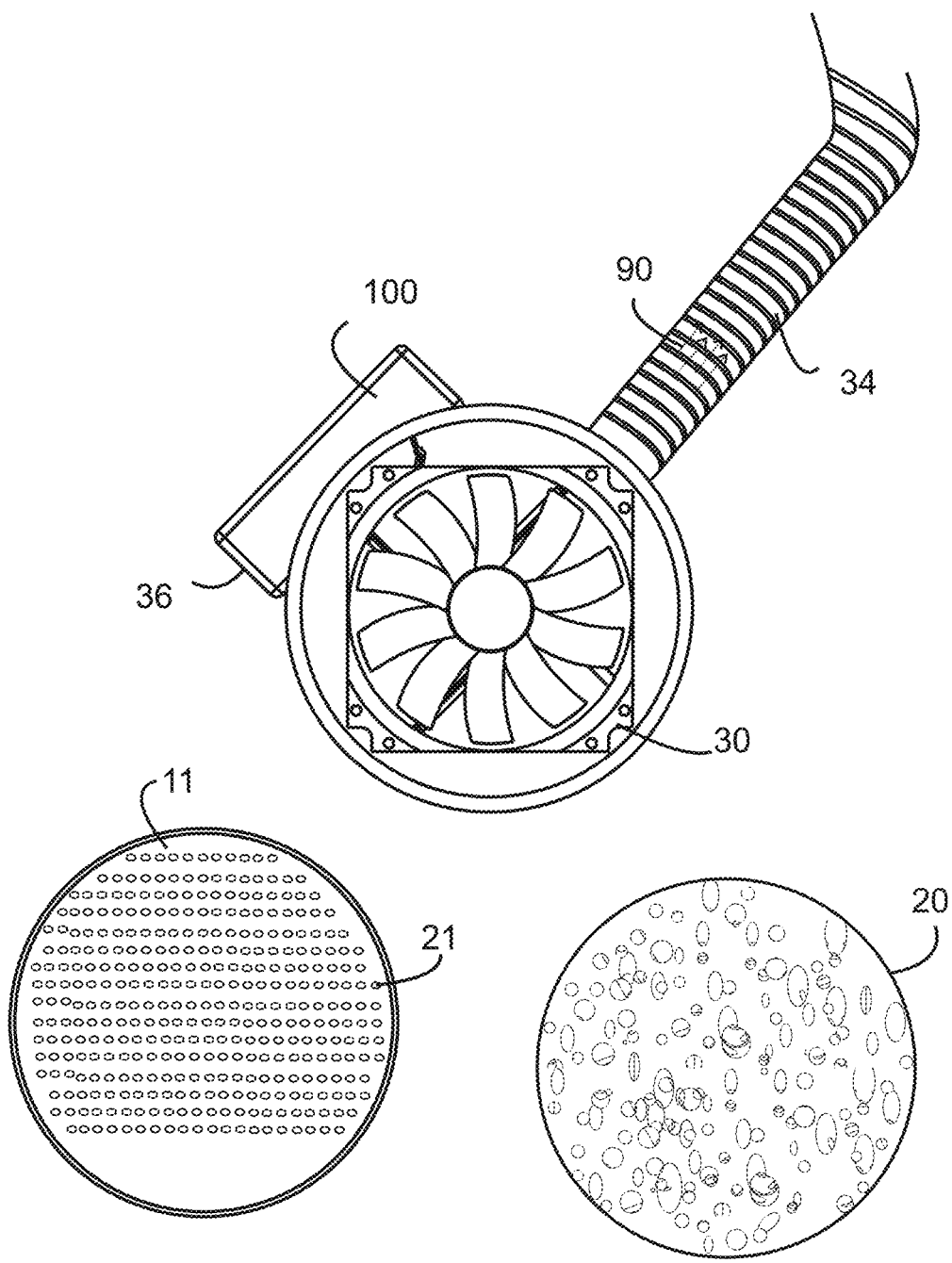
FIG. 3 is a top view of the personalized forced air purifier in open position according to the present invention.

FIG. 3 is a top elevation of the inner part of the personalized forced air purifier 10. The air fan 30 is mounted on the bottom wall 14 of the container and sucks the contaminated air through the openings 21 into the container 11. The filter 20 is inserted into the container and stands in a higher elevation from the fan 30. The contaminated air passes through the filter 20 and the pollution, dust and contaminants of the air are scrubbed by the filter 20. The purified air 90 is then diverted into the air hose 34.

Figure 4:
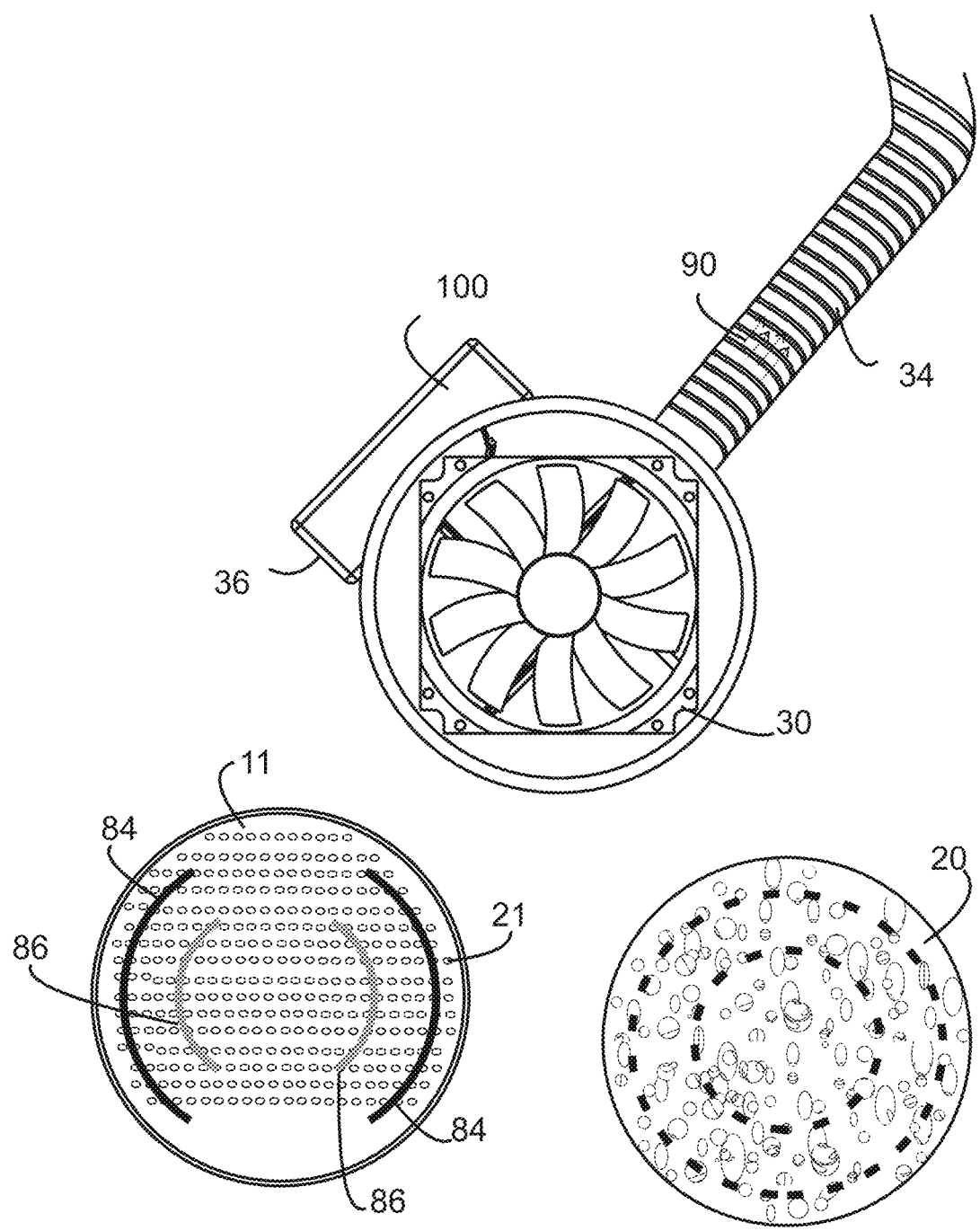
FIG. 4 is a top view of another embodiment of the present invention.
Figure 5:
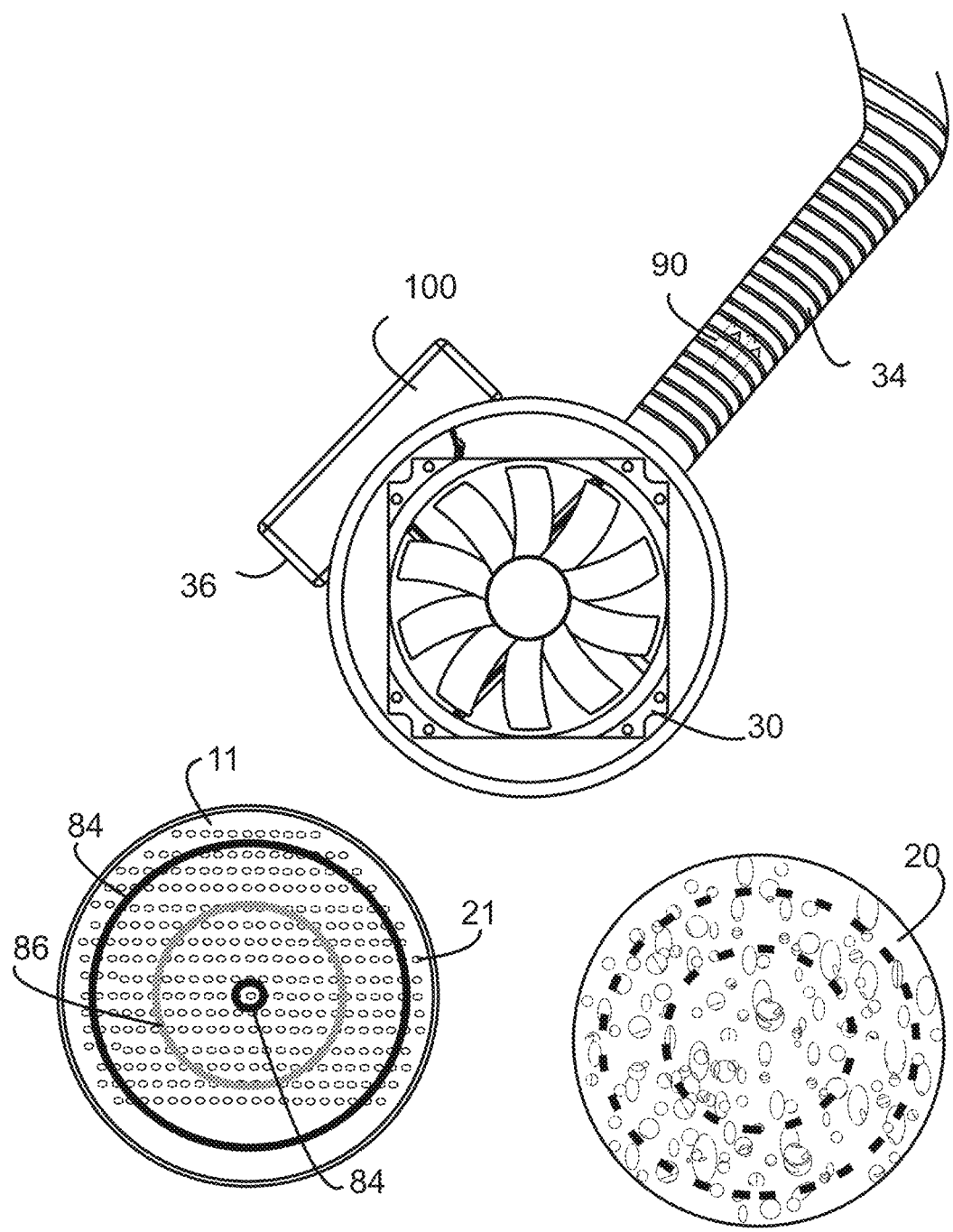
FIG. 5 is a top view of another embodiment of the present invention.

According to FIGS. 4 and 5 in another embodiment of the air purifier 10 the filtering system comprises a combination of wet filter 20 and ionization system. An ionization system is embedded inside the container 11. The ionization system comprises of a series of electrodes to produce ions and disinfect the air inside the container 11. A variety of electrode configurations can be used for purification. FIG. 4 shows two curved plate electrodes 84-86. The electrodes are from a heavy metal, such as a copper-silver alloy. Each electrode 84-86 is being connected to the power source 100. Released ions act as an electrochemical treatment to kill the bacteria released from the ambient air 40. The electrodes 84-86 can be in various configurations and the wet filter 20 is then embedded in between the electrodes.

The fan 30 sucks a significant amount of ambient air into the container 11 and pollution, dust and contaminants of the air are scrubbed by the filter 20 and neutralized by the ions. The purified air 90 is then released into the flexible hose 34 through an outlet port. The purified air is then carried towards the user's face.

Referring to FIGS. 1, 2, 3 and 4 a flexible air hose 34 is connected to the outlet port 32. The air hose 34 receives the purified air 90 and directs it to the user's face. The flexible hose 34 is connected to the outlet-port 32 from one end and to a mask or another air distribution system from another end.

Figure 6:
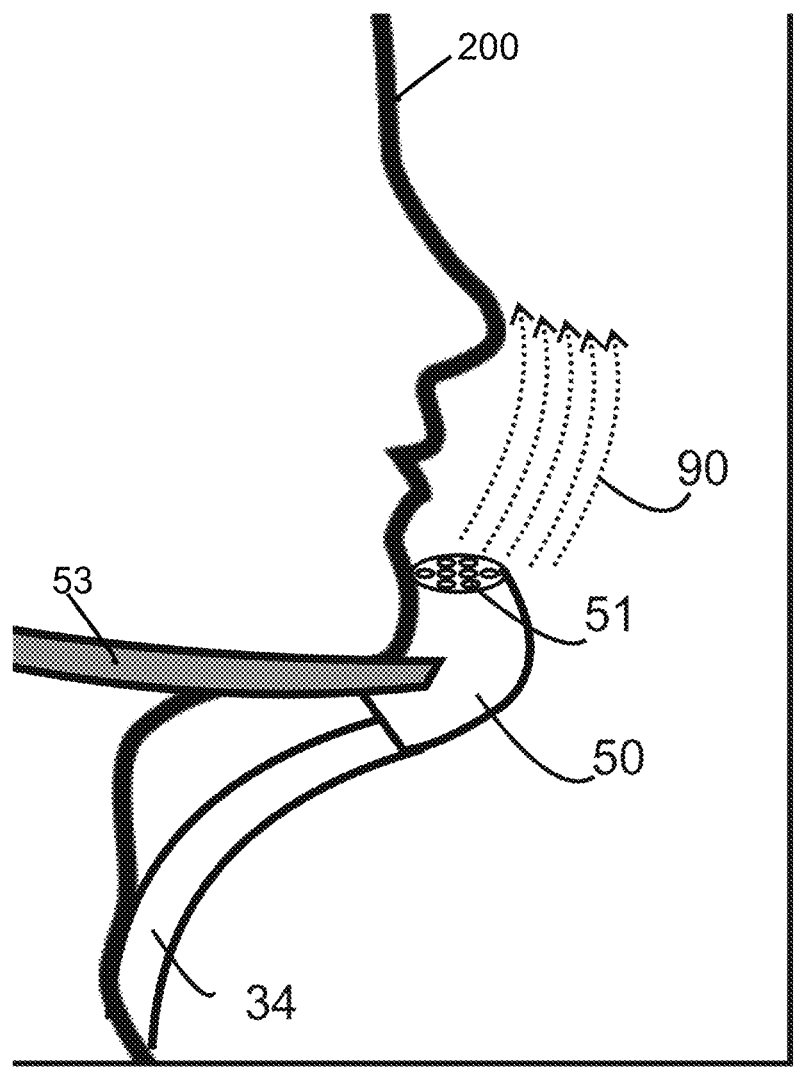
FIG. 6 is a perspective view of a chin-attaching mask according to the present invention.

The personalized forced air purifier 10 of the present invention is equipped with means to generate a flow of purified air in front of user's face. As shown in FIG. 6 said means can be a set of air jets 51 provided on a chin attaching air curtain 50. Said air curtain 50 can be attached on the chin of a user 200. Plurality of air nozzles 51 are provided on the proximal end of the flexible hose 34 and extended to the front portion of the air curtain 50. The air jets on the air curtain generate a curtain of purified air 90 in front of the nose and mouth of the user. Said air curtain 50 is attached to the user's chin using an elastic strap 53 or any other strapping means.

Figure 7:
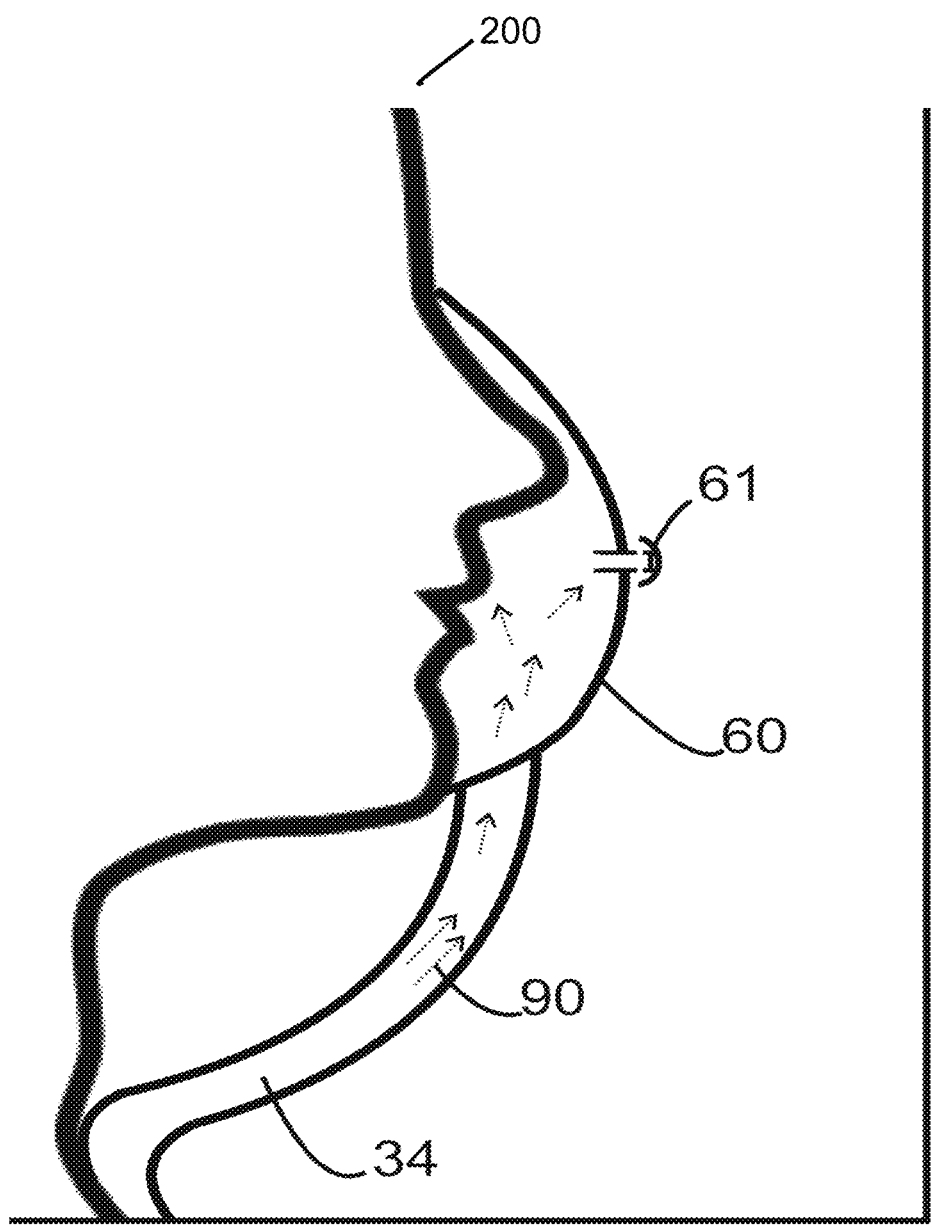
FIG. 7 is a perspective view of another type of mask portion of the present invention.

Referring to FIG. 7, air generating means can be a face mask 60 having an opening 61 in front of it. This enables the user 200 to inhale and exhale the forced purified air through the mask 60. Because the purified air is forced through the mask and there is a continuous flow of purified air in and out of the mask, the unpurified air cannot enter the mask. The purified air 90 is directed into the mask 60 through the flexible hose 34 and the exhaled air is carried out of the mask through the opening 61.

The personal air purifier 10 is made of a light weight material to be attached to a belt or hang from a neck of a user. According to FIGS. 6 and 7, the flexible hose 34 and Interface means 50-60 may comprise of rigid or resilient material or clear plastic material. Adjustable straps 53 can be used to attach the mask to the persons chin or head to allow the nose and mouth breathe the purified air 90.

Figure 8:
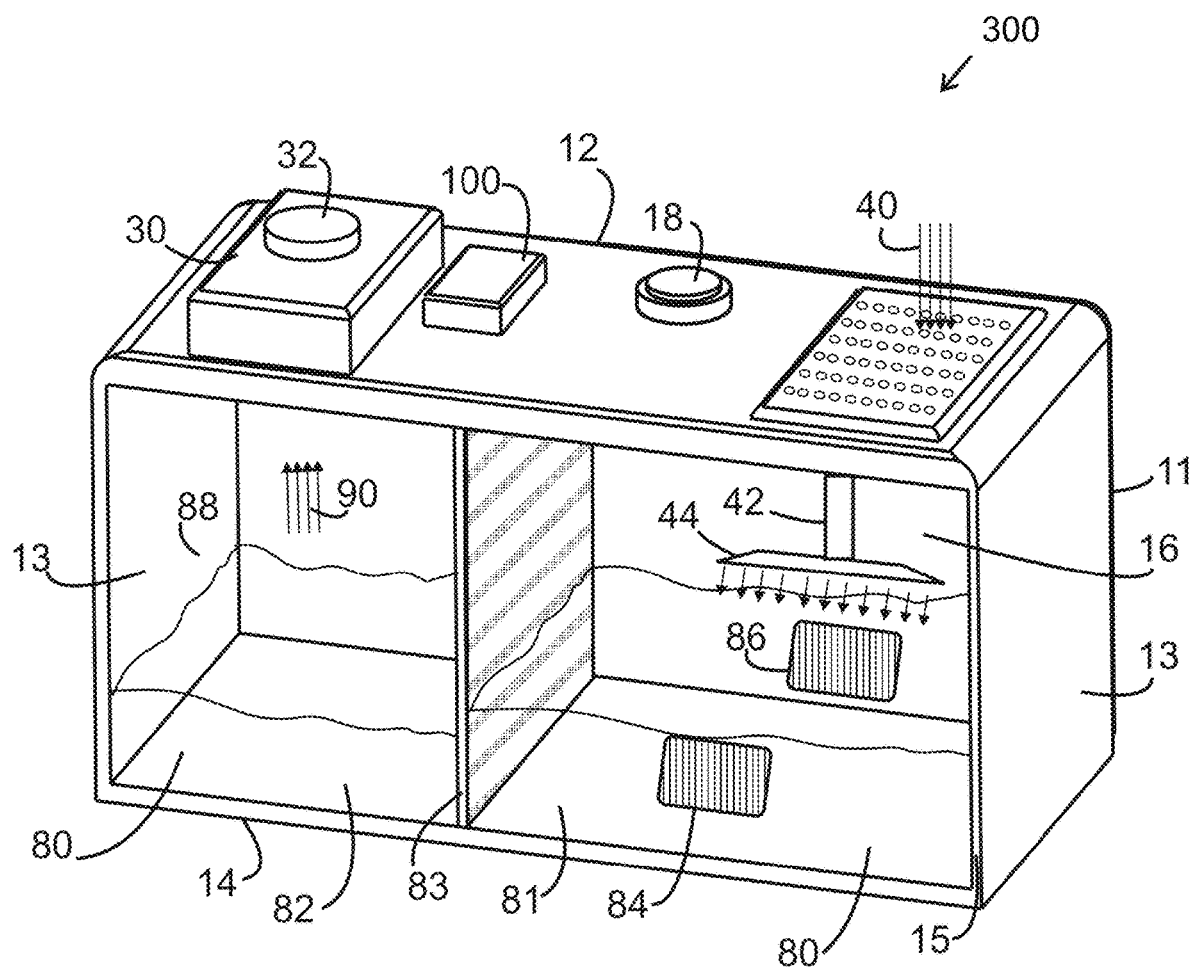
FIG. 8 is a perspective view of another embodiment of the personalized forced air purifier of the present invention.

FIG. 8 shows another embodiment of the present invention. The personal air purifier 300 comprises a container 11 having a top wall 12, a bottom wall 14, a front wall 15 and a rear wall 16 and side walls 13. Said container is divided to two sections by a filter 83 and adapted to house a volume of ionized water 80. An ionization system is embedded inside the water section 80 of the container 11. It is well known that ions of heavy metals such as copper and silver are biocidals for many bacteria. The ionization system comprises of two plate electrodes 84-86 attached to the inner walls of said compartment to ionize and disinfect the water inside the container 11. The first electrode 84 is attached to the front wall 15 of the container and the second electrode 86 is attached to the rear wall 16 of the container. The electrodes 84-86 deposit specific amount of ions into the water 80. Each electrode 84-86 is connected to the power source 100. Released ions in the water act as an electrochemical treatment to kill the bacteria released from the ambient air 40 into the water.

A battery driven air fan 30 is attached to the top wall 12 of the container. The air fan 30 sucks the ambient air 40 through openings into the container 11. The ambient air directs into the container through an air conduit 42. The air conduit 42 extends to the top of the water surface 88. A variety of air nozzles 44 can be attached to the exit of the air conduit 42 to change the air velocity impinging on the water surface 88.

Referring again to FIG. 8 again a filter 83 divides the container 11 into two compartments. The first compartment 81 is on one side of the filter 83, on the side of the air conduit 42, where the contaminated air 40 is injected. The second compartment 82 is on the other side of the filter 83, in which the air is purified. The pollution, dust and contaminants of the air are scrubbed by the water and neutralized by the ionized water. The purified air 90 entering into the clean compartment 82 is guided towards the users face.

The air fan 30 is strong enough to generate 10-15 lit/min output flow of breathing air. When this high flow air impinges on the water at the bottom of the container, it generates a significant amount of mixing and turbulence. The splashing water droplets scrub the contaminants, dust and other pollutants from the air. Any other particle that is not absorbed by the water is filtered through the filter 83. The fan 30 is battery operated to make it portable. Any type of battery driven fan can be used. Li-Ion battery driven fans are readily available which can provide sufficient air flow.

A power source 100 is provided on top wall 12 to provide power to the fan and the ionization system. Said power source is a DC battery or other suitable batteries.

The purified air 90 is then released in the second compartment 82. An outlet-port 32 is provided on top wall 12 of the second compartment 82. The flexible hose is then connected to the outlet-port 32 to carry the purified air 90 into the flexible hose and guide it to the user's interface.

As shown in FIG. 8 again an aperture 18 is provided on the top wall 12 to fill the container 11. In operation, one need only pour a measured amount of water through the aperture 18. All of the openings are positioned so as to prevent any liquid water from leaking out of the container 11. Purified air 90 is provided towards the users' face through hose, allowing for the user to breathe clean air. Ionized water which contains dust and dead bacteria will be replaced/refilled easily through the same aperture 18.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

What is claimed is:

1. A personalized forced air purifier configured to be worn by a user comprising:
   a. a container having an inlet area and an outlet area, wherein said container comprises a lid comprising the inlet area, a bottom wall comprising the outlet area, and side walls, wherein said inlet area is exposed to an ambient air;
   b. a water absorbing substance configured to absorb and retain water, said water absorbing substance configured to be placed inside said container;
   c. a set of ionization electrodes embedded inside said container and configured to generate ions inside the water of said water absorbing substance, said set of ionization electrodes are configured to ionize and disinfect the water inside said water absorbing substance;
   d. an air fan located below the bottom wall of said container, said air fan configured to suck the ambient air through said container and to exhaust a purified air;
   e. a power supply to power said air fan and said set of ionization electrodes; and
   f. a face mask configured to receive said purified air from said air fan through an air hose thereby allowing the user to breath said purified air, said face mask having an outlet port configured to let a forced air to pass through said face mask and out of the outlet port,
   whereby said set of ionization electrodes are configured to provide an electrochemical treatment of the water inside said water absorbing substance and thereby ensure that the ambient air passes through a purified water;
   wherein said water absorbing substance is located above said air fan and said water absorbing substance is embedded between said set of ionization electrodes.

2. The personalized forced air purifier of claim 1, wherein said inlet area of said lid comprises a plurality of perforations to allow the ambient air to enter said container.

3. The personalized air purifier of claim 1, wherein said set of ionization electrodes are attached to said bottom wall and extend into said container, and said water absorbing substance is located in between said set of ionization electrodes.

4. The personalized air purifier of claim 1, wherein said set of ionization electrodes comprises a plurality of pairs of ionization electrodes embedded inside said container and said water absorbing substance is configured to fit in between said set of ionization electrodes such that ionization occurs in between each pair of ionization electrodes of said set of ionization electrodes.

5. The personalized air purifier of claim 1, wherein said water absorbing substance is a sponge or a cotton.

6. The personalized air purifier of claim 1, wherein said set of ionization electrodes comprise a copper-silver alloy.

* * * * *